(12) United States Patent
Morrison et al.

(10) Patent No.: US 6,235,890 B1
(45) Date of Patent: *May 22, 2001

(54) METHODS AND COMPOSITIONS FOR THE DETECTION OF CANDIDA SPP.

(75) Inventors: Christine J. Morrison, Decatur; Errol Reiss, Chamblee; Brian Holloway, Atlanta, all of GA (US); Jong Hee Shin, Kwangju (KR)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/269,136

(22) PCT Filed: Sep. 15, 1997

(86) PCT No.: PCT/US97/16423

§ 371 Date: Jul. 12, 1999

§ 102(e) Date: Jul. 12, 1999

(87) PCT Pub. No.: WO98/11257

PCT Pub. Date: Mar. 19, 1998

Related U.S. Application Data

(60) Provisional application No. 60/026,387, filed on Sep. 16, 1996.

(51) Int. Cl.[7] .......................... C07H 21/04; C07H 21/02; C12Q 1/68; C12P 19/34
(52) U.S. Cl. .................. 536/24.33; 536/24.3; 536/24.32; 536/23.74; 536/23.1; 435/6; 435/91.1; 435/91.2
(58) Field of Search .................. 536/24.32, 23.1, 536/23.74, 24.3, 24.33; 435/7.31, 6, 810, 91.2, 91.1; 935/77, 78

(56) References Cited

U.S. PATENT DOCUMENTS

| | | | |
|---|---|---|---|
| 5,426,027 | * | 6/1995 | Lott et al. ................................. 435/6 |
| 5,631,132 | * | 5/1997 | Lott et al. ................................. 435/6 |
| 5,635,353 | * | 6/1997 | Lott et al. ................................. 435/6 |
| 5,645,992 | * | 7/1997 | Lott et al. ................................. 435/6 |
| 5,708,159 | * | 1/1998 | Ohno et al. ......................... 536/24.32 |

FOREIGN PATENT DOCUMENTS

| | | |
|---|---|---|
| 0 355 633 | 10/1989 | (EP) . |
| 0 422 869 | 4/1991 | (EP) . |
| WO 96 21741 | 7/1996 | (WO) . |

OTHER PUBLICATIONS

Ahern, H. Biochemical, Reagent Kits Offer Scientists Good Return on Investment. The Scientist vol. 9, No: 15, pp. 1–5, Jul. 1995.*

Shin J. et al., "Rapid Identification of Up to Three Candida SPP in One Reaction Tube Using Taqman PCR", Abstract of the Interscience Conference on Antimicrobial Agents and Chemotherapy, vol. 36 No. 0, Sep. 1996, p. 72.

Fujita S–I et al., "Microtitration Plate Enzyme Immunoassay to Detect PCT–Amplified DNA from Candida Species in Blood", Journal of Clinical Microbiology, vol. 33 No. 4, Apr. 1995, pp 962–97.

* cited by examiner

Primary Examiner—Stephanie W. Zitomer
Assistant Examiner—Cynthia Wilder
(74) Attorney, Agent, or Firm—Klarquist Sparkman Campbell Leigh & Whinston, LLP

(57) ABSTRACT

The present invention provides a rapid method for identifying species of Candida. Identification is through the use of a non-conserved regions of the ITS2 region flanked by highly conserved functional domains. Detection of members of the Candida and Aspergillus genera is enhanced by the detection of genus-specific regions of the 5.8S rRNA gene. The present invention provides isolated nucleic acids that selectively hybridize to the fungal genus-specific 5.8S rRNA region, and to the species-specific ITS2 region. The invention provides for nucleic acid sequences for use as selective probes for fungal genus-specific probes and as Candida species-specific probes. The present invention provides methods for the use of the Candida species-specific probes that allow the detection and identification of the individual species in biological samples.

14 Claims, No Drawings

SEQUENCE LISTING

```
<160> NUMBER OF SEQ ID NOS:  16

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: ITS1 Primer

<400> SEQUENCE: 1
tccgtaggtg aacctgcgg                                                  19

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: ITS3 Primer

<400> SEQUENCE: 2
gcatcgatga agaacgcagc                                                 20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: ITS4 Primer

<400> SEQUENCE: 3
tcctccgctt attgatatgc                                                 20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: ITS2 Primer

<400> SEQUENCE: 4
```

```
gctgcgttct tcatcgatgc                                               20

<210> SEQ ID NO 5
<211> LENGTH: 151
<212> TYPE: DNA
<213> ORGANISM: Candida albicans

<400> SEQUENCE: 5
ctccctcaaa ccgctgggtt tggtgttgag caatacgact tgggtttgct tgaaagacgg   60
tagtggtaag gcgggatcgc tttgacaatg gcttaggtct aaccaaaaac attgcttgcg  120
gcggtaacgt ccaccacgta tatcttcaaa c                                 151

<210> SEQ ID NO 6
<211> LENGTH: 124
<212> TYPE: DNA
<213> ORGANISM: Candida parapsilosis

<400> SEQUENCE: 6
ctccctcaaa ccctcgggtt tggtgttgag cgatacgctg ggtttgcttg aaagaaaggc   60
ggagtataaa ctaatggata ggttttttcc actcattggt acaaactcca aaacttcttc  120
caaa                                                               124

<210> SEQ ID NO 7
<211> LENGTH: 140
<212> TYPE: DNA
<213> ORGANISM: Candida tropicalis

<400> SEQUENCE: 7
ctccctcaaa ccccgggtt tggtgttgag caatacgcta ggtttgtttg aaagaattta    60
ccgtggaaac ttattttaag cgacttaggt ttatccaaaa cgcttatttt gctagtggcc  120
accacaattt atttcataac                                              140

<210> SEQ ID NO 8
<211> LENGTH: 231
<212> TYPE: DNA
<213> ORGANISM: Candida glabrata
<220> FEATURE:
<223> OTHER INFORMATION: All "n" refer to adenine, guanine, cytosine or
      thymine

<400> SEQUENCE: 8
ccttctcaaa cacattgtgn ttggtantga gtgatacncn nttttgatnt aacttnaaat   60
tgtaggccat atcagtatgt gggacacgag ngcaagcttc tctattaatc tgctgctgct  120
ttgcgcgagc ggcggggggtt aatactctat taggttttac caactcggtg ttgatctagg  180
gagggataag tgagtgtttt gtgcgtgctg ggcagacaga cgtctttaag t           231

<210> SEQ ID NO 9
<211> LENGTH: 177
<212> TYPE: DNA
<213> ORGANISM: Candida krusei
<220> FEATURE:
<223> OTHER INFORMATION: All "n" refer to adenine, guanine, cytosine or
      thymine

<400> SEQUENCE: 9
gagcgtcgtt tccatcttgc gcgtgcgcag agttgggtga gcggangtac cgacgtgtaa   60
agagcgtcgg agctgcgact cnnctgaaag ggagcnnant ggcccgagcg aactagactt  120
```

```
tttttnaggg nccgttttgg gccccagaac cnagttttnc cnaggncaac aaaaagn        177
```

```
<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 10
gtaaaacgac ggccag                                                     16

<210> SEQ ID NO 11
<211> LENGTH: 25
<212> TYPE: DNA
<213> ORGANISM: Candida sp.

<400> SEQUENCE: 11
agggcatgcc tgtttgagcg tcrtt                                           25

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence:Synthetic
      Probe

<400> SEQUENCE: 12
attgcttgcg gcggtaacgt cc                                              22

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence:Synthetic
      Probe

<400> SEQUENCE: 13
caaaacgctt attttgctag tggcc                                           25

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence:Synthetic
      Probe

<400> SEQUENCE: 14
ggtacaaact ccaaaacttc ttcca                                           25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence:Synthetic
      Probe

<400> SEQUENCE: 15
taggttttac caactcggtg ttgat                                           25

<210> SEQ ID NO 16
<211> LENGTH: 25
```

```
-continued
<212> TYPE: DNA
<213> ORGANISM: Artificial Sequence
<220> FEATURE:
<223> OTHER INFORMATION: Description of Artificial Sequence:Synthetic
      Probe

<400> SEQUENCE: 16
agtggcccga gcgaactaga cttt                                            25
```

METHODS AND COMPOSITIONS FOR THE DETECTION OF CANDIDA SPP.

This application claims benefit to Provisional Application No. 60/026,387 filed Sep. 16, 1996.

FIELD OF THE INVENTION

This invention relates to diagnostic assays for the detection and differentiation of the genus Candida and different species of Candida as well as other microorganisms, and compositions and kits for performing the assays.

BACKGROUND OF THE INVENTION

*Candida albicans* is a commensal of the gastrointestinal tract. *C. albicans*, and to a lesser extent several other related species, are of increasing importance as opportunistic pathogens in immunocompromised hosts. A dimorphic, diploid yeast with no known sexual cycle, *C. albicans* is an endogenous organism that can be isolated from skin and mucosal tissues of persons whose immune systems are intact. However, perturbations of the immune or endocrine systems can create opportunities for Candida species to convert from a commensal state to invade tissues either locally or systemically. An example of this opportunism is the oral-esophageal or vaginal candidiasis that is encountered in association with HIV infection.

In *C. albicans*, the nuclear rDNA genes encoding the 5S, 18S, 5.8S, and 28S rRNAs are found as 50–100 copy tandem repeats of approximately 10 kb unit length on chromosome seven (Magee et al., 1987, Thrash-Bingham and Gorman, 1992). The 5S rDNA gene (121 bp) is flanked by two nontranscribed regions located between the small and large subunits, and collectively termed the intergenic spacer (IGS). Ribosomal 5.8S sequences have been compiled from a variety of eukaryotes (Dams et al., 1988). In addition, sequence analysis of the 5.8/28S internally transcribed spacer (ITS) region has shown strain variation within at least one fungal species (O'Donnell, 1992), while other species have demonstrated complete conservation (Mitchell et al., 1992). Strain-specific restriction polymorphisms (RFLPs) have previously been observed in the IGS region for *C. albicans* (Magee et al., 1987).

An opportunistic fungus, *C. albicans* also causes systemic disease in severely immunocompromised hosts. It is the most causative species of disseminated candidiasis followed by *C. tropicalis, C. parapsilosis,* and *C. glabrata* (Odds, 1988). Dissemination occurs when Candida is spread via the bloodstream or by invasion of mucosal surfaces to internal organs (Odds, 1988). High-risk patient populations include individuals with malignancy or neutropenia, those receiving chemotherapy and/or multiple antibiotics, and those with indwelling catheters or low birth weight infants (Armstrong, 1989).

Diagnosis of systemic candidiasis is complicated by the absence of clinically distinguishing signs, frequently negative blood cultures, and the absence of a reliable serological test to detect infection. Currently, disseminated candidiasis is often diagnosed by a minimum of at least two positive blood cultures (Odds, 1988). However, blood culture alone is clearly not sufficient for the diagnosis of disseminated candidiasis since as many as 50% of disseminated candidiasis cases are diagnosed at autopsy (Telenti, et al. 1989). The nephrotoxicity of amphotericin B, the drug of choice for immunocompromised patients with disseminated disease, precludes its use for prophylaxis.

The incidence of disseminated candidiasis has increased in recent years due to the rising number of immunosuppressed and post-operative patients. The advent of new anti-fungal drugs has improved the prospects for management of this disease; however, diagnosis remains difficult. In addition, although fluconazole prophylaxis of bone marrow transplant patients has reduced the incidence of disseminated disease caused by *Candida albicans*, other Candida species which are innately resistant to fluconazole, most notably *C. krusei* and *C. glabrata*, have increased as the primary causative agent. Early detection and identification of Candida species is therefore essential for the proper targeting of antifungal therapy.

These facts, in conjunction with the difficulty of reliably culturing Candida from the blood and the lack of a sensitive and specific serological test to detect disease, underscore the need to develop alternative diagnostic approaches.

Technology has been developed for the detection of bacterial and viral DNA from the bloodstream of infected patients through the use of the polymerase chain reaction (PCR). The PCR amplifies genomic DNA geometrically so that it may be detected by agarose gel electrophoresis, Southern blotting, or dot blot hybridization (Miyakawa et al. 1992, Kafatos et al. 1979, Lasker et al. 1992).

PCR-based diagnostic methods may provide increased sensitivity relative to blood culture techniques since viable organisms are not required for amplification or detection. There has only been one report to date describing the detection of *C. albicans* cells in infected patient blood through the use of PCR-amplified DNA (Buckman et al. 1990). Buchman et al. lysed *C. albicans* cells with ZYMOLYASE and proteinase K and extracted the DNA with phenol and chloroform. The limit of sensitivity by this method was 120 cells per ml of whole blood. As described, this method was time consuming, labor-intensive, repeatedly used toxic chemicals (phenol and chloroform), and has not been shown to be readily reproducible. In addition, a single copy gene, the cytochrome P-450 gene, was the target for DNA amplification, thus making the method much less sensitive. Miyakawa et al. described improved sensitivity by use of Southern blot hybridization for the detection of PCR products from Candida DNA (Miyakawa et al. 1991). The limit of sensitivity by Southern blot in their study was 10 cells per ml of urine and did not address detection in blood.

Use of polymerase chain reaction (PCR)-based tests to detect *C. albicans* DNA in body fluids has produced some encouraging results. However, routine application of these tests for the detection of candidemia remains difficult. Current methods require labor-intensive sample preparation, costly enzymes for liberation of Candida DNA, and phenol-chloroform extraction to purify DNA before PCR amplification. After amplification, detection of PCR products by gel electrophoresis or Southern blotting is often not practical in a clinical laboratory setting. Sensitivity has been variable and false positive as well as false negative results have been reported. Also, most studies have concentrated on the detection of *C. albicans* DNA but not on DNA from non-albicans Candida species.

On the other hand, routine, culture-based identification of Candida species requires at least one day following initial positive results to obtain a pure culture, another day to identify *C. albicans* isolates by germ tube formation, and two or more additional days to identify non-albicans Candida isolates by API-20C sugar assimilation strip tests and cornmeal agar morphology. Therefore, a test to rapidly and accurately identify Candida isolates to the species level would be both clinically and epidemiologically useful.

The ability to detect Candida in blood is crucial for the rapid and accurate diagnosis of systemic candidiasis, because detection from urine or mucosal secretions can be confused with the normal commensal status of the organism or a localized non-disseminated infection.

SUMMARY OF THE INVENTION

The invention provides a rapid approach to species identification through the use of non-conserved regions of the ITS2 flanked by highly conserved, functional domains. Genus and other related organism identification is also enhanced by detection of "genus"-specific regions of the 5.8S rRNA gene. It was surprising to find a region of this gene which enabled us to selectively retrieve the organisms described here.

The present invention provides an isolated double-stranded nucleic acid consisting essentially of the nucleotide sequence defined in the Sequence Listing by SEQ ID NO:5. This is the *C. albicans* ITS2 sequence and includes a nucleic acid comprising a nucleotide sequence that is specific for *C. albicans*. Further examples of an isolated double stranded nucleic acid of the present invention consist essentially of the nucleotide sequences defined in the Sequence Listing by SEQ ID NOs:6–9. These are the ITS2 sequences for *C. parapsilosis, C. tropicalis, C. glabrata* and *C. krusei*. These nucleic acids can include a nucleotide sequence that is specific for the respective organism.

The present invention further provides an isolated double stranded nucleic acid consisting essentially of the sequence set out in Table 1 and referred to as "ALL-CAN-TET" and its complement. Nucleic acid sequences which specifically hybridize with this sequence, particularly the first four base pairs (AGGG) or their complement, is indicative of a number of Candida spp., if not all, and *Saccharomyces cerevisiae* and at least two Aspergillus species all as indicated on Table 4. These organisms are opportunistic pathogens and knowledge of their presence can provide useful treatment information. Detection for both Aspergillus and Candida is important because they tend to appear under the same circumstances such as in bone marrow transplant patients. Treatment is similar whether one or the other or both genera are detected.

An isolated nucleic acid that specifically hybridizes with or selectively amplifies a nucleic acid of the invention or fragments thereof is also contemplated. An isolated nucleic acid complementary to the above nucleic acid is also provided.

A method of diagnosing systemic candidiasis in a subject is also provided. The method comprises the steps of: (a) collecting blood from the subject into tubes containing detergent, polypropylene glycol, sodium polyanetholesulfonate, and sodium ethylene diamine tetraacetic acid; (b) lysing Candida cells using ZYMOLASE-100T with agitation; (c) extracting and precipitating the DNA from the lysed cells; (d) amplifying the precipitated DNA using universal fungal primer pairs derived from the internal transcribed spacer regions of the Candida ribosomal DNA; and (e) detecting amplified DNA from Candida by hybridizing the amplified DNA with a probe that selectively hybridizes with Candida DNA, the presence of amplified DNA indicating systemic candidiasis.

DEFINITIONS

Unless defined otherwise, all technical and scientific terms used herein have the same meaning as commonly understood by one of ordinary skill in the art to which this invention belongs. Singleton et al. (1994) *Dictionary of Microbiology and Molecular Biology*, second edition, John Wiley and Sons (New York); Walker (ed) (1988) *The Cambridge Dictionary of Science and Technology*, The press syndicate of the University of Cambridge (New York); and Hale and Marham (1991) The Harper Collins Dictionary of Biology Harper Perennial (New York) all provide one of skill with a general dictionary of many of the terms used in this invention. Although any methods and materials similar or equivalent to those described herein can be used in the practice or testing of the present invention, certain preferred methods and materials are described. For purposes of the present invention, the following terms are defined below.

The terms "isolated" or "biologically pure" refer to material which is substantially or essentially free from components which normally accompany it as found in its native state.

The term "nucleic acid" refers to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence optionally includes the complementary sequence thereof.

Two single-stranded nucleic acids "hybridize" when they form a double-stranded duplex. The region of double-strandedness can include the full-length of one or both of the single-stranded nucleic acids, or all of one single stranded nucleic acid and a subsequence of the other single stranded nucleic acid, or the region of double-strandedness can include a subsequence of each nucleic acid. An overview to the hybridization of nucleic acids is found in Tijssen (1993) *Laboratory Techniques in Biochemistry and Molecular Biology—Hybridization with Nucleic Acid Probes* Part I Chapter 2 "Overview of principles of hybridization and the strategy of nucleic acid probe assays", Elsevier (New York).

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen, supra. Generally, highly stringent wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ point for a particular probe. Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

The term "identical" in the context of two nucleic acid sequences refers to the residues in the two sequences which are the same when aligned for maximum correspondence. A nucleic acid is "substantially identical to a reference nucleic acid when it is at least about 70% identical, preferably at least about 80% identical, and optionally about 90% identical or more.

The term "primer" as used herein refers to an oligonucleotide, whether occurring naturally as in a purified restriction digest, or produced synthetically, and is capable of hybridizing to a strand of the target sequence. When the terminal 3' nucleotide has hybridized it acts as a point of initiation of synthesis under conditions in which synthesis of an extension of the primer is induced. These conditions typically include the presence of four different nucleotide triphosphates (a nucleotide reagent) and thermostable enzyme in an appropriate buffer and at a suitable temperature. When primer pairs are referred to herein, the pair is meant to include one primer which is capable of hybridizing to the sense strand of a double-stranded target nucleic acid (the "sense primer") and one primer which is capable of hybridizing to the antisense strand of a double-stranded target nucleic acid (the "antisense primer"). The primer pair will be designed such that they flank the region of the target nucleic acid to be amplified and will cause the target region to be amplified when placed in an amplification protocol such as polymerase chain reaction.

What is meant by a primer "substantially homologous" or "substantially complementary" to a nucleotide sequence is a polynucleotide or oligonucleotide containing naturally occurring nucleotides or their analogs, such as 7-deazaguanosine or inosine, sufficiently complementary to hybridize with the target sequence such that stable and specific binding occurs between the primer and the target sequence. The degree of homology required for formation of a stable hybridization complex (duplex) varies with the stringency of the amplification medium. The primer should be substantially homologous to the target strands of each specific sequence to be amplified. This means that the primer must be sufficiently complementary to hybridize with the appropriate strand under standard amplification conditions. Therefore, the primer sequence need not reflect the exact sequence of the template. For example, a noncomplementary nucleotide fragment may be attached to the 5' end of the primer, with the remainder of the primer sequence complementary to the strand. Alternatively, noncomplementary bases or longer sequences can be interspersed into the primer provided that the primer sequence has sufficient complementarity with the sequence of the target sequence to hybridize with it and thereby form a template for synthesis of the extension product.

DETAILED DESCRIPTION OF THE INVENTION

The present invention provides an isolated double-stranded nucleic acid consisting essentially of the nucleotide sequence defined in the Sequence Listing by SEQ ID NO:5. This includes the *C. albicans* ITS2 sequence. By "isolated" is meant separated from other nucleic acids found in the naturally occurring organism. The nucleic acid comprises a nucleotide sequence that is specific for *C. albicans*. By "specific" is meant a sequence which does not hybridize with other nucleic acids to prevent determination of an adequate positive hybridization with nucleic acids from *C. albicans*. Probes which "specifically hybridize" with the double-stranded nucleic acid are hybridizing with one of the two strands when in single stranded form.

A further example of an isolated double stranded nucleic acid of the present invention consists essentially of the nucleotide sequence defined in the Sequence Listing by SEQ ID NO:6. This includes the ITS2 sequence for *C. parapsilosis*. This nucleic acid comprises a nucleotide sequence that is specific for *C. parapsilosis*.

Another example of the isolated double stranded nucleic acid of the invention consists essentially of the nucleotide sequence defined in the Sequence Listing by SEQ ID NO:7. This includes the *C. tropicalis* ITS2 sequence. This nucleic acid comprises a nucleotide sequence that is specific for *C. tropicalis*.

A still further example of the isolated double stranded nucleic acid of the invention consists essentially of the nucleotide sequence defined in the Sequence Listing by SEQ ID NO:8. This includes the *C. glabrata* ITS2 sequence. This nucleic acid comprises a nucleotide sequence that is specific for *C. glabrata*.

Another example of the isolated double stranded nucleic acid of the invention consists essentially of the nucleotide sequence defined in the Sequence Listing by SEQ ID NO:9. This includes the *C. krusei* ITS2 sequence. This nucleic acid comprises a nucleotide sequence that is specific for *C. krusei*.

Another example of an isolated double stranded nucleic acid of the invention consists essentially of the nucleotide sequence referred to herein as All-CAN-TET and defined in the Sequence Listing by SEQ ID NO:11. This nucleic acid comprises a nucleotide sequence that is specific for all *Candida* spp., *Saccharomyces cerevisiae*, *Aspergillus fumigatus*, and *Aspergillus flavus*, but not other fungal, bacterial or human DNA tested as described below in Table 4. If Aspergillus sp. are to be detected for, it is desired that the sample be subjected to mechanical disruption to release Aspergillus nucleic acid.

An isolated nucleic acid that specifically hybridizes with or selectively amplifies a nucleic acid of the invention or fragments thereof is also contemplated. An isolated nucleic acid complementary to the above nucleic acid is also provided. The sequences can be selected based on the nucleotide sequence and the utility of the particular sequence. More specifically the invention provides isolated nucleic acids that specifically hybridize with the nucleic acids consisting essentially of the nucleotide sequences defined in the Sequence Listing by SEQ ID NOs:5–9.

Oligonucleotides for use as primers or probes are typically synthesized chemically according to the solid phase phosphoramidite triester method described by Beaucage and Caruthers (1981), *Tetrahedron Letts.*, 22(20):1859–1862, e.g., using an automated synthesizer, e.g., as described in Needham-VanDevanter et al. (1984) *Nucleic Acids Res.*, 12:6159–6168. Oligonucleotides can also be custom made and ordered from a variety of commercial sources known to persons of skill. Purification of oligonucleotides, where necessary, is typically performed by either native acrylamide gel electrophoresis or by anion-exchange HPLC as described in Pearson and Regnier (1983) *J. Chrom.* 255:137–149. The sequence of the synthetic oligonucleotides can be verified using the chemical degradation method of Maxam and Gilbert (1980) in Grossman and Moldave (eds.) Academic Press, New York, *Methods in Enzymology* 65:499–560.

One of skill will also recognize many ways of generating alterations in a given nucleic acid sequence. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, Giliman and Smith (1979) *Gene* 8:81–97; Roberts et al. (1987) *Nature* 328:731–734 and Sambrook et al. (1989) *Molecular Cloning—A Laboratory Manual* (2nd Ed) Vol. 1–3; Innis, Ausbel, Berger, Needham VanDevanter and Mullis (all supra).

The primers of use in the assay methods described here are preferably single stranded for maximum efficiency and amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of an enzyme. The exact lengths of the primers will depend on many factors, including temperature, source of primer and use of the method. Most typically, amplification primers are between 8 and 100 nucleotides in length, and preferably between about 10 and 30 nucleotides in length. More typically, the primers are between about 18 and 28 nucleic acids in length.

Probes of the invention to detect for individual species or genus will be of a length sufficient to specifically hybridize with and result in the specific isolation of the targeted sequence. These probes will be about 4 to about 234 base pairs in length, preferably about 8 to about 35 base pairs in length, and most preferably about 15 to about 22 base pairs in length. Examples of probes for individual Candida spp. which are five base pairs in length are as follows:

C. albicans: CAAAC or TTCAA or CTTCA
C. parapsilosis: AAATT or CAAAT or CAAAA
C. tropicalis: ATAAC or TTCAT or TCATA
C. glabrata: TAACT or TTAAG or AAGTT
C. krusei: ATTAC or TCATA or CATAA The term "consisting essentially of", as used herein includes modifications to the nucleic acids of the invention as long as the specificity (genus or species) of the nucleic acids is maintained. Likewise, fragments used as primers or probes can have substitutions so long as enough complementary bases exist for specific hybridization (Kunkel et al. *Methods Enzymol.* 1987:154:367, 1987).

The nucleic acid can have homology with nucleotide sequences present in more than one Candida species. Such a nucleic acid sequence shared with other Candida species can be used, for example, as a primer to simultaneously amplify nucleic acids from more than one Candida species. The amplified nucleic acids can then be detected using the specific nucleic acids described herein to permit either genus specific or species specific diagnosis. Thus, the specific nucleic acid can be specific for the genus Candida and can be used to detect any candidiasis in methods such as polymerase chain reaction, ligase chain reaction and hybridization.

A method of diagnosing systemic candidiasis in a subject is also provided. The method comprises the steps of: (a) collecting blood from the subject into tubes containing detergent, polypropylene glycol, sodium polyanetholesulfonate, and disodium ethylene diamine tetraacetic acid ((Na)$_2$EDTA); (b) lysing Candida cells using ZYMOLASE-100T with agitation; (c) extracting and precipitating the DNA from the lysed cells; (d) amplifying the precipitated DNA using universal fungal primer pairs derived from the internal transcribed spacer regions of the Candida ribosomal DNA; and (e) detecting amplified DNA from Candida by hybridizing the amplified DNA with a probe that selectively hybridizes with Candida DNA, the presence of amplified DNA indicating systemic candidiasis.

In the method, the lysis step can use the lysis buffer from the ISOQUICK® kit in addition to ZYMOLASE-100T. The agitation step can be by rocking at about 16 cycles per minute. The extracting step can use the extraction matrix in the ISOQUICK® kit. In the amplification step of the above method, one of the primers of the primer pair is derived from the internal transcribed spacer 1 (ITS1) and the other primer of the primer pair is derived from the internal transcribed spacer 2 (ITS2). Alternatively, one of the primers of the primer pair is derived from the internal transcribed spacer (ITS3) and the other primer of the primer pair is derived from the internal transcribed spacer 4 (ITS4). The detecting step hybridization can be by dot blot hybridization using a genus or species specific Candida probe.

In the method of detecting systemic candidiasis, the DNA that is amplified can be from C. albicans and the probe can specifically hybridize with a specific nucleotide sequence of the nucleic acid of SEQ ID NO:5 as described in Example 2. By using the other specific nucleic acids as provided herein, the method of Example 2 can be used to detect any of the other Candida species as taught herein. If the DNA that is amplified is from C. parapsilosis, the probe specifically hybridizes with a specific nucleotide sequence of the nucleic acid of SEQ ID NO:6. If the DNA that is amplified is from C. tropicalis, the probe specifically hybridizes with a specific nucleotide sequence of the nucleic acid of SEQ ID NO:7. If the DNA that is amplified is from C. glabrata, the probe specifically hybridizes with a specific nucleotide sequence of the nucleic acid of SEQ ID NO:8. If the DNA that is amplified is from C. krusei, the probe specifically hybridizes with a specific nucleotide sequence of the nucleic acid of SEQ ID NO:9. A nucleic acid having homology with more than one Candida species can also be used as a probe that specifically hybridizes with Candida DNA to detect systemic candidiasis.

Additionally, it is contemplated that the nucleic acids (e.g., probes and primers) can be attached to or labeled with (covalently or non-covalently) a detectable moiety. The probes may be suitably labeled using, for example, a radio label, enzyme label, fluorescent label, biotin-avidin label and the like for subsequent visualization in the example of the dot blot hybridization procedure taught in Example 2. An example of such a labeled nucleic acid is the digoxigenin-UTP labelled probe provided in Example 2, although others can be readily generated using standard methods (See, e.g., Sambrook et al., 1989). The nucleic acids specific for a given Candida species can each be labeled with a distinct detectable moiety, such that species specific probes for several species can be used with the same sample of amplified DNA to permit species specific diagnosis. The distinct label for each species specific probe can be detected in the sample if DNA from the particular species is present in the subject.

The detection of fungal DNA as described herein can also be performed using a ligase chain reaction (LCR). Essentially, this reaction, known to those of skill in the art, involves the use of, for each region to be detected, two primers that hybridize to the same strand of the target DNA, either abutting each other or with one or two nucleotides between the two primer sequences (i.e., "immediately 5'" or "immediately 3'" to the junction). The ligase reaction is performed, and the products are electrophoresed through a gel that can detect very small fragments, such as an SDS-polyacrylamide gel. A positive result is one in which a product equal in size to the sum of the two primers is produced, as this indicates the presence of all of the target DNA region. It is preferable that three reactions be run in three separate tubes, targeted at detecting (1) the first junction, (2) the second junction and (3) an internal sequence as a positive LCR control. If one wants to electrophorese all LCR products together through the gel, primers must be carefully chosen such that their individual sizes can be distinguished from the predicted size of any LCR products. Alternatively, the product of each reaction can be electrophoresed separately. Primers are preferably exactly homologous to the target region and of a size between approximately 20–40 nucleotides.

Kits

Further contemplated are kits for the assays and detection of organisms described here. Combinations of reagents useful in the methods set out above, particularly any of the probes or primers, can be packaged either singly or together with instructions for using them in the described assays. A preferred kit would contain the probes set out in Table 1 and instructions for performing the assay with a single test aliquot.

The following examples are intended to illustrate, but not limit, the invention. While they are typical of those that might be used, other procedures known to those skilled in the art may be alternatively employed.

EXAMPLES

Example 1

Nucleotide Sequence Analysis of the ITS2 Region of *Candida albicans* and Related Species Yeast strains and maintenance All Candida isolates have been previously characterized by assimilation (API) profiles and morphology (Van der Walt and Yarrow, 1984). In addition, all *C. albicans* and *C. parapsilosis* isolates have previously been electrophoretically karyotyped and are known to represent distinct, non-related strains (Lasker et al., 1989). All isolates were grown and maintained on yeast-peptone-dextrose (YPD) medium (Guthrie and Fink, 1991). For DNA extractions, 10 ml of overnight cultures grown on YPD at 37° C. were washed twice in 1×TE buffer and the DNA extracted by standard procedures (Sambrook et al., 1989). Prior to PCR amplifications, DNA was digested with EcoRI restriction endonuclease (New England Biolabs), electrophoresed on 1.0% agarose gels, and stained with ethidium bromide (EtBr) to verify concentration and purity.

PCR amplification and DNA sequencing

Taq polymerase, buffers, and conditions for PCR were those supplied by the vendor (Perkin-Elmer/Cetus), using 100 ng genomic DNA per reaction. For primary amplifications, 35 cycles of 95° C., 55° C., and 72° C. at one min. intervals were followed by a five min. final extension at 72° C. The following "universal" ITS primers were used, for which calculated Tm's have previously been reported (White et al., 1990):

ITS1 5' TCC GTA GGT GAA CCT GCG G 3' (SEQ ID NO:1)

ITS3 5' GCA TCG ATG AAG AAC GCA GC 3' (SEQ ID NO:2)

ITS4 5' TCC TCC GCT TAT TGA TAT GC 3' (SEQ ID NO:3)

Primer ITS1 is to a conserved 3' domain in the 18S nuclear subunit. Primer ITS3 is approximately 25 bp from the end of the 5.8S subunit, and ITS4 is a reverse primer to a conserved region of the nuclear large rDNA. In addition, a −21M13 forward primer sequence (Messing et al. 1981) was added at the 5' end to primers ITS1 and ITS4 for sequencing in the forward and reverse directions, respectively, and consisted of the sequence:

5' GTA AAA CGA CGG CCA G 3' (SEQ ID NO:10)

where the terminal 5' T of ITS1 and ITS4 made 17 bp of the 18 bp annealing sequence. From preliminary experiments it was determined that the addition of this sequence did not alter the nature of the derived PCR product. The aqueous phase of the primary PCR reaction was ethanol-precipitated, dried, and resuspended in 8 μl TE buffer. The entire amount was loaded into single wells of a 1.5% agarose, 1.0% NuSieve agarose gel (Lehmann et al. 1992), electrophoresed at 110 V., and stained with EtBr. Single, intensely staining bands of the appropriate size were excised and the DNA was extracted in Spin-X cellulose acetate columns (Costar, Inc.) for 30 min. at 40° C., 13000×g. The DNA was then ethanol-precipitated, washed twice in 70% EtOH, dried briefly, and resuspended in $H_2O$ for sequencing. Automated DNA sequencing (Smith et al. 1986), was performed using the Applied Biosystems Catalyst 800 workstation, with the "Prism" dye-primer dideoxy-sequencing reactions (Sanger et al. 1977), using conditions supplied by the vendor (Applied Biosystems). The precipitated DNA was dried and resuspended in 6 μl of formamide/50 mM EDTA (5:1), denatured for 2 min. at 90° C., and loaded on an Applied Biosystems model 373A DNA sequencer. All DNAs were sequenced in both forward and reverse orientations, and multiple runs were performed for all species and most strains within a given species.

5.8s rDNA 5.8S sequence alignments were performed both manually and with the "pileup" program from the University of Wisconsin Genetics Computer Group (GCG) package (Devereux et al., 1984). ITS alignments were performed in all possible pairwise combinations using the Needleman and Wunsch algorithm as implemented by GCG (Needleman and Wunsch 1970). DNA parsimony and bootstrap analysis was performed using the "Phylip" programs of Felsenstein (Felsenstein 1982), implemented on a micro-vax (Digital Equip. Corp.) cluster. Dendrograms were constructed using the global option and using a variety of different species as the outgroup (Felsenstein 1985). Other 5.8S sequences were: *Neurospora crassa, Schizosaccharomyces pombe, Saccharomyces cerevisiae, Pneumocystis carinii, Fusarium sambucium, Epichloe typhina, Cephalosporium acremonium, Lentinula edodes.*

For *C. albicans* and *C. parapsilosis*, where multiple strains were analyzed, there was complete nucleotide conservation within the entire 159 bp 5.8S region. The greatest degree of diversity for the species used in this study was found in the two relatively unconserved regions between bp 79–85 and bp 118–136. The overall average degree of diversity between the Candida species was approximately three percent. The minimum degree of diversity was found between *C. tropicalis* and *C. parapsilosis*, with a single C-A transversion at bp 62. Interestingly, both *C. albicans* and *C. krusei* contained A-G transitions in the termination consensus TCATTT.

A phylogenetic analysis was performed with all known fungal 5.8S sequences using strict parsimony as implemented by Felsenstein and statistical bootstrap analysis (Felsenstein 1982; 1985). *P. carinii* was used as the outgroup considering previous findings based on 18S analysis using a larger database of eukaryotic organisms (Edman et al. 1988). There were a total of 47 informative sites for the number of fungal sequences compiled, including 4 single base pair gaps. Re-analysis of the data set without gaps did not significantly alter the tree topology. The cumulative number of positive selections out of 100 total iterations is given for each branch point. The derived tree does not differ significantly from previous research using a weighted difference algorithm for 18S sequences, and supports the view that these species are related such that *C. albicans, C. parapsilosis* and *C. tropicalis* are more closely aligned than *C. krusei* within a clade. Likewise, *C. glabrata* appears more distantly related and can equally be placed at a number of positions within the larger branch of yeast-like fungi. It is generally accepted that values of 70 or greater out of 100 randomly tested samples will represent similar trees to a significant degree of probability.

ITS2 rDNA

The sequences of the ITS2 regions for *C. albicans, C. parapsilosis, C. tropicalis, C. glabrata* and *C. krusei* are shown in the Sequence Listing as SEQ ID NOs:5–9.

A total of ten *C. albicans* isolates, representing typical and morphologically (or physiologically) atypical strains, were found to be identical at the nucleotide level within the ITS region. Similarly, five strains of *C. parapsilosis*, displaying a wide range of electrophoretic karyotypes and randomly amplified polymorphisms (RAPD), were also identical to the type strain for the species. The entire length of the ITS region was found to be species specific.

Similar to the results of the 5.8S alignments, we found that *C. albicans, C. parapsilosis*, and *C. tropicalis* were also most homologous in this ITS region. This homology extended for the first 57 bp 51 immediately adjacent to the termination of the 5.8S sequence. In contrast, the 3' region displayed little homology. For *C. krusei* and *C. glabrata* there was no apparent homology either to each other or to members of the *C. albicans* group over this entire ITS region. Sequences were aligned in all possible pairwise combinations (Needleman and Wunsch 1970), and the average degree of similarity was found to be approximately 40 percent.

Analysis of the ITS2 region has revealed that *C. albicans*, and possibly other closely related species, displays no inter-strain variation. In this respect this species resembles the opportunistic fungus *Cryptococcus neofornans*, and is unlike the plant pathogen *Fusarium sambucinum* which displays variation in this region.

Example 2

Detection of DNA from *Candida albicans* Cells in Blood by Use of the Polymerase Chain Reaction (PCR) Growth of *C. albicans*

*C. albicans* strain 36B was grown on Sabouraud's dextrose agar Emmons slants for 48 h at 25° C. Cells were harvested by washing each slant with 5 ml of 0.85% NaCl, centrifuged at 1500×g for 10 min, and resuspended to the appropriate concentration in freshly collected rabbit's blood or 0.85% saline.

Yeast cell lysis and DNA purification

Blood from adult female rabbits (New Zealand White, Myrtle's Rabbit Farm) was collected from the central ear artery into ISOLATOR 10® microbial tubes (Wampole Laboratories, Cranbury, N.J.) containing an aqueous solution of 1 unit of purified saponin, 8 ml/L polypropylene glycol, 9,6 g/L Na polyanetholesulfonate and 16 g/L (Na)$_2$EDTA; EDTA-coated tubes (Becton Dickinson, Rutherford, N.J.); or heparinized tubes (Becton Dickinson). *C. albicans* strain 36B (Quebec Gynecological Institute, Montreal, Quebec) cells were then introduced and samples were centrifuged at 3000×g for 30 min. Supernatants were removed and an equal volume of deionized water was added to lyse residual blood cells. Remaining *C. albicans* cells were washed in 0.85% NaCl and pelleted by centrifugation at 1500×g for 10 min. ISOLATOR 10® tubes have proven superior to other blood collection systems for the recovery of viable *C. albicans* cells from blood (Jones, 1990). The use of the ISOLATOR 10® tubes for blood collection resulted in PCR amplification of candidal DNA whereas the use of EDTA- or heparin-coated tubes did not.

*C. albicans* DNA was extracted and purified using the ISOQUICK® nucleic acid extraction kit according to the manufacturer's instructions with the addition ZYMOLASE-100T, to allow its use with fungi, since the ISOQUICK® kit was developed by MicroProbe Corporation for the isolation and purification of DNA from only mammalian cells and gram negative bacteria. Briefly, pelleted cells were suspended in 100 μl of sample buffer for 15 min after which 100 μl of lysis buffer was added. The mixture was incubated at 25° C. for 1 h. Selected samples contained zymolyase (ZYMOLYASE-100T, Seikagaku Corp., Tokyo, Japan; 5 mg/ml in 1.0 M sorbitol, 0.1 M trisodium citrate, and 0.1% 2-mercaptoethanol) during the lysis step and were rocked at 16 cycles per min to optimize breakage of *C. albicans* cells. The addition of zymolyase to the lysis step allowed for successful adaptation of the ISOQUICK® kit for use with *C. albicans* cells. Alternatively, *C. albicans* cells were disrupted using a mini bead beater (Biospec Products, Bartlesville, Okla.) (Glee et al. 1987). Cells (1 ml) were delivered into Sarstedt microfuge tubes containing 1 ml of 0.5 mm diameter glass beads and beaten at maximum speed for 2 min. A third method released *C. albicans* DNA by boiling $1 \times 10^7$ cells per ml in 2 mls of deionized water in an Eppendorf microcentrifuge tube for 30 min. Mechanical disruption of *C. albicans* cells by bead beating or boiling was less effective in producing PCR amplifiable DNA; these methods may be too harsh, resulting in shearing or fragmentation of DNA. For precipitation of the DNA sodium acetate and other components of the ISOQUICK® kit were used as directed.

After lysis, DNA was purified with the extraction matrix provided in the ISOQUICK® kit, precipitated with sodium acetate in the presence of isopropanol, and the precipitated DNA was dried by vacuum centrifugation for 15 min.

PCR amplification of genomic DNA

Universal fungal primer pairs, ITS1 and 2 or ITS3 and 4, synthesized by the CDC core facility., and the GeneAmpR DNA amplification reagent kit using native Taq DNA polymerase (250 U, Perkin Elmer Cetus, Alameda, Calif.) were used for PCR amplification of genomic DNA (Saiki et al. 1988). These primers amplify DNA from all fungi and some parasites. Examples of the ITS1, ITS2, ITS3 and ITS4 primers are shown in the Sequence Listing as SEQ ID NOs:1, 4, 2 and 3, respectively. The reaction consisted of the following: 53.5 μl of double distilled, sterile water, 10 μl of 10× reaction buffer, 16 μl of a mixture of equimolar (1.25 mM) quantities of DATP, dCTP, dGTP, and dTTP, 5 μl of 20 μM ITS1 or 3, 5 μl of 20 μM ITS2 or 4, 10 μl of target DNA, 0.5 μl of Taq polymerase, and 6 μl of 25 mM MgCl$_2$. Samples were overlaid with mineral oil prior to placement in the thermal cycler (Perkin Elmer Cetus) to minimize evaporation during DNA amplification. Samples were initially denatured in the thermal cycler at 95° C. for 5 min. This was followed by 30 cycles of: denaturation at 95° C. for 1 min, annealing at 50° C. for 2 min, and extension at 72° C. for 1.5 min. Final extension occurred at 72° C. for 5 min.

After amplification, mineral oil was discarded. An equal volume of chloroform was added to the samples which were then centrifuged for 5 min at 4100×g to extract residual mineral oil. The aqueous layer was removed and the DNA precipitated from it by adding 2 volumes of ice-cold 100% ethanol followed by incubation for 30 min at −70° C. Samples were then centrifuged for 1 min at 4100×g, the ethanol removed, the samples dried under vacuum, and resuspended in 20 μl of TE buffer (20 mM Tris plus 1 mM EDTA, pH 8.0). Amplified DNA was visualized after agarose (1% agarose plus 1% Nu-Sieve in TE buffer) gel electrophoresis by ethidium bromide staining or by dot blot hybridization analysis.

Dot blot hybridization

*C. albicans* strain 3307 DNA was used as a probe for the dot blot. To make the probe, 20 ng of *C. albicans* 3307 genomic DNA was PCR-amplified using ITS1 and ITS2 or ITS3 and ITS4 as primer pairs. The PCR product was then electrophoresed on an agarose gel and the resultant DNA band cut out of the gel. The product was extracted from the gel by the freeze-squeeze method of Thuring et al (Thuring et al., 1975). The DNA probe was labeled by incubating overnight with digoxigenin-dUTP from a nonradioactive-DNA labeling and detection kit according to the manufacturers instructions ("Genius" kit, Boehringer Mannheim, Indianapolis, Ind.). Other genus or species specific probes derived from the nucleic acids of SEQ ID NOs:5–9 can also be used in this method.

Samples were prepared for the dot blot (Kafatos et al., 1979, Lasker et al., 1992) by diluting 10 µl of *C. albicans* DNA to 25 µl with TE buffer, adding NaOH to a final concentration of 0.3 M, and incubating for 10 min at 25° C. All equal volume of 2.0 M ammonium acetate was then added to each sample on ice. Each sample was then dotted under vacuum onto a nitrocellulose filter using a dot blot apparatus (BioRad, Richmond, Calif.) according to the manufacturer's instructions. The filter was then removed from the apparatus and dried at 80° C. under vacuum for 2 h. The dried filter was placed in a plastic bag, sealed, and prehybridized with single-stranded salmon sperm DNA (10 µg/ml) overnight in a 65° C. water bath.

The digoxigenin-labeled probe was denatured by boiling for 5 min, added to the filter in the plastic bag, and placed in a 65° C. water bath overnight. The filter was then washed twice for 30 min each in citrated saline (0.3 M NaCl with 0.03 M sodium citrate, pH 7.0) and 0.1% SDS at 60° C. (Lasker et al., 1992). Washed filters were incubated for 30 min at 25° C. with an anti-digoxigenin antibody (1:5000) labeled with alkaline phosphatase. Chromogen (nitroblue tetrazolium salt and 5-bromo-4-chloro-3-indolyl phosphate) was added (Lasker et al., 1992) and color developed for 6 h at 25° C. in the dark.

"Booster" PCR amplification

"Booster" PCR amplification was performed by the method of Ruano et al. (Ruano et al., 1989). Briefly, the same protocol as outlined above was used, but after 15 cycles of PCR amplification, samples were removed from the thermal cycler and fresh primers were added to a final concentration of 40 µM. The samples were then returned to the thermal cycler for 15 additional cycles and final extension. The level of sensitivity of detection of the PCR product from cells introduced into blood was improved from $10^5$ cells per ml to $10^3$ cells per ml as detected by ethidium bromide stained agarose gels. However, the specificity of this system was poor since the negative control became positive.

Detection of PCR amplified products from *C. albicans* in saline by agarose gel electrophoresis A comparison of *C. albicans* DNA isolated and purified from saline using the ISOQUICK® kit alone to that obtained by the use of zymolyase plus the kit was performed. *C. albicans* cells ($10^7$/ml saline) were lysed at either 37° C. or 25° C. The combined use of zymolyase and the ISO-QUICK® kit (at either 25° C. or 37° C.) resulted in enhanced recovery of purified DNA relative to the kit alone.

To determine the sensitivity of the zymolase plus ISO-QUICK® method for cell breakage and DNA purification, *C. albicans* cells were then serially diluted in saline ($10^7$ to $10^1$ cells per ml) before breakage. Ethidium bromide stained agarose gels demonstrated that $10^3$ cells per ml could be detected by this method. Based on these results, all subsequent experiments used zymolyase followed by DNA purification with the ISOQUICK® kit at 25° C.

Detection of PCR amplified products of *C. albicans* in blood by agarose gel electrophoresis To determine if the zymolyase plus ISOQUICK® kit method could be used to detect *C. albicans* in blood, $10^7$ *C. albicans* cells per ml was introduced into freshly collected rabbit's blood as described above. Blood was collected into one of the following: ISOLATOR 10® microbial tubes, EDTA-coated tubes, or heparinized tubes. Amplified DNA was detected in the samples prepared from cells introduced into blood drawn into ISOLATOR 10® tubes only. No DNA was detected in samples where blood had been drawn into either only EDTA- or only heparin-coated tubes.

The sensitivity of detection for *C. albicans* DNA in blood using the zymolyase plus ISOQUICK® kit method was determined by serially diluting *C. albicans* cells ($10^7$ to $10^1$ cells per ml) in blood drawn into ISOLATOR 10® tubes. Using agarose gel electrophoresis and ethidium bromide staining, $10^5$ cell per ml could be detected.

Dot blot hybridization for detection of PCR amplified products of *C. albicans* in blood or saline In an effort to improve the sensitivity for detection of *C. albicans* DNA, a comparison was performed of the ethidium bromide-stained agarose gel method to a dot blot hybridization method for the detection of the PCR product. The dot blot method allowed detection of $10^1$ cells per ml in saline versus $10^3$ cells per ml detected by agarose gel electrophoresis and ethidium bromide staining. The sensitivity for detection of the PCR product of *C. albicans* cells introduced into blood was $10^1$ cells per ml by the dot blot method versus $10^5$ cells per ml for ethidium bromide stained agarose gels detection. The probe used for the above dot blot was *C. albicans*-specific. *C. tropicalis* DNA and human placental DNA did not react in the dot blot, supporting the specificity of the probe. Thus, the methods taught herein are capable of detecting Candida DNA in clinical samples such as blood.

Universal fungal primers as described herein provide the potential for amplification of DNA from all fungi. However, by using a *C. albicans*-specific DNA probe, as in the above-described dot blot hybridization step, the test was specific for *C. albicans*. The dot blot assay can be conducted using specific probes for other Candida species, as described herein, or other fungi. Furthermore, because the present method can gently extract DNA from clinical samples, the method can also use viral, bacterial or other fungal primers for the PCR reaction followed by specific DNA probes for each genus or species in the dot blot as described above.

Example 3

Detection of DNA from Candida SPP. in Blood by Use of the Polymerase Chain Reaction Detection and identification of Candida spp. has become particularly important because of an increase in newly emerging, non-albicans Candida infections. We used fungus-specific PCR primers and species-specific DNA probes to detect up to three Candida spp. in one reaction tube (TaqMan™ PCR, Perkin-Elmer Corp., Foster City, Calif.). Probes to the internal transcribed spacer region of rDNA were labeled with one of three fluorescent reporter dyes: FAM (6-carboxy-fluorescein), TET (tetrachloro-6-carboxy-fluorescein), or HEX (hexa-chloro-6-carboxy-fluorescein). Each dye emits a characteristic wavelength upon PCR amplification of specific target DNA so that up to three probes can be used simultaneously during the PCR reaction. A different signal for each probe is then detected immediately after thermal cycling by using a fluorescent microtiter plate reader. Six probes were used in this study: CA-FAM, CT-TET, and CP-HEX were added to one tube for the simultaneous detection and identification of C. albicans, C. tropicalis, and C. parapsilosis, respectively. TG-FAM and CK-TET were added to a second tube for C. glabrata and C. krusei detection (fluconazole-resistant species). AllCAN-TET, a Candida genus probe, was added to a third tube. DNA recovered from 61 positive blood culture bottles, including 23 C. albicans, 18 C. glabrata, 6 C. tropicalis, 6 C. krusei, 5 C. parapsilosis, and 3 mixed fungemias, were used. Control samples included bacteremia (n=10) or other fungemia (n=3) cultures, or bottles with no growth (n=10). TaqMan™ PCR detected and correctly identified 57 of 61 specimens (93.4%) and gave no false-positive results. This method is rapid, eliminating post-PCR hybridization and incubation steps. It is sensitive and specific for detecting and identifying Candida spp. from blood culture bottles, allowing for earlier diagnosis and appropriate targeting of drug therapy.

We describe a clinically useful PCR-based method for rapid detection and identification of Candida isolates from positive blood culture bottles. A simple extraction method using heat, detergent, and mechanical breakage was used to obtain Candida DNA for PCR amplification without use of expensive enzymes or phenol-chloroform. A simple, rapid, and sensitive microtiter plate format and fluorescently labeled probes with different emission wavelengths were used to detect up to three Candida species simultaneously. This method eliminated an additional post-PCR hybridization step since fluorescent probes annealed to the target DNA during PCR amplification and reduced time to species identification from a mean of 3.5 days by conventional methods to 5 h by our method.

Clinical samples

A total of 81 samples from cultured BacT/Alert bottles (organon Teknika Corporation, Durham, N.C.) were tested. Ten milliliters of blood from patients with suspected bacteremia or fungemia were collected at the bedside, and 5 ml each was immediately inoculated into an aerobic and an anaerobic BacT/Alert bottle. Inoculated bottles were agitated continuously in the BacT/Alert instrument (Organon Teknika Corporation, Durham, N.C.) at a rate of 68 cycles per min and were incubated at 35° C. for 5 d or until bottles were positive by calorimetric detection of $CO_2$. Aliquots from positive bottles were Gram stained and subcultured. Bottles proven to contain Candida spp. by Gram staining were selected and 2 ml aliquots were removed and stored at −30° C. During the study period, Candida spp. were isolated from 61 culture bottles from 24 patients.

Of 61 bottle sets from which Candida spp. were isolated, C. albicans blastoconidia were isolated from 23 bottles, C. glabrata from 18 bottles, C. tropicalis from 6 bottles, C. krusei 6 bottles, C. parapsilosis from 5 bottles and mixed C. glabrata and C. albicans from 3 bottles. Ten randomly selected samples from patients with bacteremia due to coagulase-negative Staphylococci (n=2), Enterococcus spp. (n=2), Citrobacter freundii (n=2), Corynebacterium JK (n=1), Corynebacterium, non-JK (n=1), or due to a mixture of Enterococcus spp. and S. aureus (n=1), or Klebsiella pneumoniae and A. calcoaceticus (n=1), were also tested as negative controls. Clinical specimens which never became positive during incubation (n=10) were also tested as negative controls.

In addition to clinical samples, BacT/Alert bottles spiked with C. albicans strain B311 at 0, $10^1$, $10^2$, $10^3$, $10^4$, and $10^5$ blastoconidia per 200 µl of rabbit whole blood were tested (broth to rabbit blood ratio=8:1).

Extraction of DNA

A mechanical disruption method was used. Two hundred microliters of sample was added to 800 [il of TXTE buffer (10 mM Tris, 1 mM EDTA, pH 8.0, 1% Triton X-100) in a sterile, 1.5 ml centrifuge tube and incubated for 10 min at RT. After lysis, cell debris and Candida blastoconidia were pelleted by centrifugation at 14,000 rpm for 5 min in an Eppendorf centrifuge (Eppendorf model 5403, Germany). After three washes by centrifugation with 1 ml of TXTE buffer, the pellet was resuspended with 300 µl of TXTE buffer and transferred to a 2 ml screw-cap conical-bottom tube containing 200 µl of 0.5 mm zirconium beads (Biospec Products, Bartlesville, Okla.). After boiling for 15 min, the mixture was shaken for 20 min in a mechanical cell disrupter (Mini-beadbeater, Biospec Products). After centrifugation for 20 sec, the supernatant was stored at −20° C. until used for PCR amplification.

Purified DNA

Purified Candida DNA (Fujita et al) including C. albicans, C. tropicalis, C. parapsilosis, C. glabrata and C. krusei DNA were used as the template standard for each TaqMan® PCR. These DNAs and purified DNA from other Candida species, Saccharomyces cerevisiae, Cryptococcus neoformans, Aspergillus fumigatus, A. flavus, Penicillium marneffei, Histoplasma capsulatum, Blastomyces dermatitidis, Staphylococcus aureus, Escherichia coli, Pseudomonas aeruginosa and a human placental cell line, were obtained by conventional means as previously described (Fujita, et al). All strains of microorganisms used were described previously except for C. lusitaniae strains and C. peudotropicalis strain, WO 696, which were from the CDC mycology reference laboratory.

Fluorescent probe design and synthesis

Probes consisted of oligonucleotides, labeled at the 5' end with one of three available fluorescent reporter dyes; FAM (6-carboxy-fluorescein), TET (tetrachloro-6-carboxy-fluorescein) or HEX (hexachloro-6-carboxy-fluorescein). Probes also contained a quencher dye, TAMRA (6-carboxy-tetramethy-rhodamine), attached to a linker-arm-modified nucleotide near the 3' end and a 3'-blocking phosphate. The six probes used in this study are listed in Table 1: All-CAN-TET to detect all Candida spp., and CA-FAM, CT-TET, CP-HEX, CG-FAM and CK-TET to detect C. albicans, C. tropicalis, C. parapsilosis, C. glabrata and C. krusei DNA, respectively.

TaqMan® PCR

PCR was performed using primers ITS3 and ITS4 (Fujita, et al) and a modification of a previously published PCR protocol (Fujita et al) by using TaqMan® fluorescently-labeled probes. Based upon G+C content, the predicted melting temperatures (Tms) of the CA, CG, CP, CK, and CT probes (Fujita et al) were 70° C., 70° C., 70° C., 76° C. and 72° C. In addition, a probe to detect all Candida species was designed from the 5.8s region of rDNA (All-CAN probe, Tm=80° C.). On the other hand, the Tms of the ITS 3 and 4 primers were 62° C. and 58° C. Since PCR amplification with ITS primers is carried out in the presence of the fluorescently-labeled Candida probes, probes were re-designed so that Tms would optimize primer extension and allow multiple probes to bind with similar frequency when admixed in one reaction tube.

Three sets of probe mixtures were designed. First, CA-FAM, CT-TET, and CP-HEX were added simultaneously to the PCR mixture for the detection and identification of *C. albicans, C. tropicalis* and *C. parapsilosis*, respectively (PCR "A"). Second, probes CG-FAM and CK-TET were added to the PCR mixture for the detection and identification of *C. glabrata* and *C. krusei* (innately fluconazole-resistant strains; PCR "B"). Third, the All-CAN-TET probe was used to detect all Candida spp. (PCR "C"). PCR was performed on a 1 µl sample in a total of 50 µl volumes containing 10 mM Tris-HCl, 50 mM KCl (pH 8.3), $MgCl_2$ (from 2.5 to 5.0 MM), 0.2 mM (each) dNTP, 0.2 µM of each primer, 2.5 U of Taq DNA polymerase (Boehringer Mannheim, Germany) and one, two or three fluorescent probes (10 to 50 nM final concentration). A two-step PCR using a combined annealing and extension temperature was performed in a Perkin Elmer 9600 thermocycler (Emeryville, Calif.). All cycles began with a DNA denaturation step for 5 min at 94° C. After this, cycles consisted of 30 s at 95° C. (denaturation) and 90 s at 58° C. (annealing and extension) for 40 cycles. Other two-step cycles used consisted of 30 s at 95° C. and 1 min at 58° C. for 45 cycles. Primer extension, at 72° C. for 10 min, followed the final cycle.

Negative controls (no template control) were carried out using the same reaction mix under the amplification conditions described but in the absence of template. Positive standards for multiplex PCR used 1 ng of purified DNA for each Candida spp. to be detected.

Fluorescent detection of TaqMan® PCR

Either immediately or within 24 h (samples stored in a dark refrigerator) following PCR, 40 µl of each PCR product was transferred to a clean, white 96-well microtitration plate designed for the detection of fluorescence (Perkin-Elmer). Forty µl of TE buffer (10 mM Tris, 1 mM EDTA, pH 8.0) was used as a buffer blank. The plate was read on a Perkin-Elmer LS 50B Luminescence Spectrometer with a microtitration plate reader attachment. The excitation wavelength used was 488 nm. The emission wavelength for each reporter dye was as follows: FAM, 518 nm; TET, 538 nm; HEX, 556 nm. The emission wavelength for the quencher dye (TAMRA) was 582 nm. The excitation slit width was 488 nm, and the emission slit width was 10 nm. Fluorescent data management system using EXCEL-compatible macros were used for data analysis.

Data analysis and interpretation

PCR using All-CAN-TET probe for the detection of all Candida spp

Using the TaqMan® data worksheet and macro, the delta RQ for each sample was automatically calculated. The delta RQ is an increase in the emission intensity ratio of the reporter dye after release from the quencher dye on the TaqMan® probe (RQ+) minus the baseline emission intensity of the quenched reporter dye on the intact TaqMan® probe (RQ−). A threshold RQ is calculated to assure a statistically high confidence level (99%) using the standard deviation obtained from triplicate, no template control samples. We established a cutoff value for positivity to be 3SD above the mean delta RQ for all negative controls (n=20) used in this study.

TaqMan® PCR using two or three fluorescent probes simultaneously

We used the multicomponented data program for interpretation of TaqMan® PCR results. The multicomponented data program automatically showed the results as 'No DNA', template 1 (or allele 1), template 2 (allele 2), or template 3 (allele 3) when either the TaqMan® 3 Allele-Genotype Worksheet or the 2-reporter multicomponent worksheet for WPR (wellplate reader software) was used. The No DNA threshold was automatically calculated from values for 2 SD above the mean (value=1.00) of the negative controls. We normalized no DNA values as 'DNA values' by subtracting each no DNA value from 1. We established cutoff values for the DNA value as 1 SD above the mean for control values and for each probe, as 2 SD above the mean for control values in TaqMan® PCR reactions.

Quality control

Each reaction was carried out in duplicate or triplicate. One nanogram of *C. albicans* and *C. glabrata* DNA was used as positive controls for each sample run. Carry over was eliminated by using aerosol-resistant pipet tips and separate laboratory areas for DNA sample preparation and PCR amplification.

RESULTS

Optimization of TaqMan® PCR

Probes used for the TaqMan® PCR assays are shown in Table 1. We evaluated the effect of $MgCl_2$ concentration, extension time, number of PCR cycles and probe concentration on delta RQ values. The optimal magnesium ion concentration was determined by testing concentrations from 2.5 nM to 5.0 nM, using 40 cycles consisting of 30 s at 95° C. and 90 s at 58° C. The delta RQ was highest when a $MgCl_2$ concentration of 3.5 nM was used (4.37±0.38, n=4; range 3.33 to 5.16). This $MgCl_2$ concentration range did not change the (RQ−) values (0.71 to 0.84).

Using a constant PCR mixture composition, we then compared the effects of PCR extension time and cycle number on delta RQ values. No increase in delta RQ values were obtained when 45 cycles and a 1 min extension time (delta RQ=3.33±0.45, n=2) was used compared to 40 cycles with 90 s extension time (delta RQ=3.46±0.13, n=2). All experiments therefore used 40 cycles and a 1 min extension time. Concentration of each probe was optimized by testing concentrations from 10 to 50 nM. Optimum probe concentrations were: All-CAN-TET, 25 nM; CA-FAM, CT-TET and CG-FAM, 10 nM. In TaqMan® PCR for simultaneous detection and identification of *C. albicans, C. tropicalis* and *C. parapsilosis* (PCR "A"), and in TaqMan® PCR using CG-FAM and CK-TET probes for simultaneous identification of *C. glabrata* and *C. krusei* (PCR "B"), the delta RQ was highest when a probe concentration of 10 nM was used. Therefore, probes were used at 10 nM concentrations for TaqMan® PCR.

Delta RQ values were consistently higher for probes labeled with FAM, followed by those labeled with TET, followed by those labeled with HEX. When different batches of the CK probe were labeled with one of the three fluorescent labels, the mean delta RQ for FAM-labeled CK probes was 1.34±0.04 (n=3), while that for the TET-labeled CK probe was 0.61±0.27 (n=6) and for the HEX-labeled CK probe was 0.30±0.01 (n=3).

Sensitivity and specificity of the TaqMan® PCR assay for clinical samples

Among 61 clinical samples from patients with 10 candidemia, 58 samples were proved to contain a single Candida spp. (Table 2). The mean delta RQ values using the All-CAN-TET probe against homologous spp. were: *C. albicans*, 3.42±0.67 (range=1.15 to 4.58); *C. tropicalis*, 1.92±1.34 (range=0.45 to 3.48); *C. parapsilosis*, 1.78±1.48 (range=0.80 to 4.22); *C. glabrata*, 2.81±1.24 (0.53 to 4.66); and *C. krusei* 3.38±0.92 (1.87 to 4.40) (Table 3). Delta RQ values for the All-CAN-TET probe using three samples identified as mixed cultures of both *C. glabrata* and *C. albicans* were 4.14, 3.46, and 3.58, respectively.

The mean delta RQ values for Candida species-specific probes against homologous species were: CA-FAM for *C. albicans* isolates, 0.95±0.62 (n=23); CT-TET for *C. tropicalis* isolates, 0.48±0.38 (n=6); CP-HEX for *C. parapsilosis* isolates, 0.37±0.12 (n=5); CG-FAM for *C. glabrata* isolators, 0.63±0.39 (n=18); and CK-TET for *C. krusei* isolates, 0.73±0.33 (n=6) (Table 3). Specimens tested by the PCR "A" assay were considered positive when the DNA value was above 0.16 (1 SD), the delta RQ was above 0.7 (2 SD) for the CA-FAM probe, above 0.13 (2 SD) for the CT-TET probe, and above 0.19 (2 SD) for the CP-HEX probe. The sensitivity and specificity of the PCR "A" assay was therefore 91.9% (34/37) and 100% (44/44), respectively.

Specimens tested by the PCR "B" assay were considered positive when the DNA value was above 0.15 (1 SD), the delta RQ was above 0.04 (2 SD) for the CG-FAM probe, and above 0.08 (2 SD) for the CK-TET probe. The sensitivity and specificity of the PCR "B" assay (to detect fluconazole-resistant Candida spp.) was therefore 96.3% (26/27) and 100% (54/54), respectively.

Specimens tested by the PCR "C" assay were considered positive when the delta RQ value was above 0.25 (3 SD). The sensitivity and specificity of the PCR "C" assay (to detect all Candida spp.) was therefore 100% (61/61) and 100% (20/20), respectively (Table 3).

Detection and identification of Candida spp. by PCR with fluorescent probes

PCR-EIA identification (Fujita et al) of Candida spp. from 61 blood cultures of 24 patients with candidemia were identified as: *C. albicans* (n=23), *C. glabrata* (n=18), *C. parapsilosis* (n=5), *C. tropicalis* (n=6), *C. krusei* (n=6), and mixed candidemias due to *C. albicans* and *C. glabrata* (n=3). The PCR "C" assay, using the All-CAN-TET probe, detected all Candida spp in all 61 samples. The PCR "A" and "B" assay results matched those for the PCR-EIA for 55 of the 58 samples reported to contain a single Candida spp. (b 23 *C. albicans*, 17 *C. glabrata*, 4 *C. parapsilosis*, 5 *C. tropicalis*, and 6 *C. krusei*). Two of three samples identified as mixed candidemia specimens by conventional and by PCR-EIA were also identified to contain both *C. glabrata* and *C. albicans* but one mixed candidemia was identified as *C. glabrata* only (*C. albicans* was not detected) by the PCR "A" and "B" assays (Table 2).

Five *C. albicans*-positive bottles revealed the coexistence of *C. albicans* with bacteria including Enterococcus spp. (n=4) and coagulase-negative Staphylococci (n=1). All were correctly identified to contain *C. albicans*. Ten randomly selected samples from patients with bacteremia were all negative by TaqMan® PCR (Table 3).

Therefore, PCR using the All-CAN-TET probe detected all Candida spp. (100%) and TaqMan® PCR assays "A" and "B" rapidly and correctly identified all Candida spp. in 57 (93.4%) of 61 clinical blood cultures (Table 2). Sensitivity and specificity of the All-CAN-TET probe The All-CAN-TET probe detected all Candida spp., *S. cerevisiae*, *A. fumigatus* and *A. flavus*, but no other fungal, bacterial or human DNA tested (Table 4). Although purified Aspergiflus spp., DNA was detected with the All-CAN-TET probe, the mechanical sample preparation method used did not release Aspergillus DNA from intact cells. Therefore, a different sample preparation method would need to be used to obtain Aspergillus DNA from clinical samples and only Candida and *S. cerevisiae* DNA would be expected to be detected in clinical materials processed as described in this paper.

TaqMan® PCR sensitivity

We compared Taqman® PCR results with those from a PCR-EIA method developed in our laboratory (Fujita et al) using *C. albicans blastoconidia* suspended in BacT/Alert culture bottles inoculated with rabbit blood. *C. albicans* strain B311 blastoconidia were introduced at concentrations of 0, $10^1$, $10^2$, $10^3$, $10^4$, or $10^5$ per 200 µl of BacT/Alert blood culture broth containing whole rabbit blood (broth to rabbit blood ratio=8:1).

The mean delta RQ values for the All-CAN-TET probe for each 200 µl sample in three experiments was 3.10±0.45 for $10^5$ cells, 2.75±0.18 for $10^4$ cells, 0.69±0.12 for $10^3$ cells, and 0.34±0.07 for $10^2$ cells (Table 5). The sensitivity of detection by EIA was therefore $10^2$ cells per 200 µl of sample, or 1 cell per 2 µl sample relative to control samples containing no *C. albicans blastoconidida* (P<0.01). This was equal to the detection limit of the PCR-EIA method. The detection limit by EtBr staining was ten-fold lower than either method ($10^3$ cells per 200 µl of sample).

The detection limit for TaqMan® PCR using CA-FAM, CT-TET and CP-HEX probes were $10^3$ Cells per 200 µl of sample, or 10 cells per 2 µl of sample. This represented a ten-fold lower sensitivity than the PCR-EIA method and equal sensitivity to detection by EtBr staining of agarose gels (Table 5).

TABLE 1

Probes used for TaqMan ® PCR assay

| Probes | Nucleotide Sequence (5' to 3') and Chemistry |
|---|---|
| AII-CAN-TET | SEQ ID NO: 11 5'TET AG GGC ATG CCT GTT TGA GCG TC(GA) TT-3'-P |
| CA-FAM | SEQ ID NO: 12 5'FAM AT TGC TTG CGG CGG TAA CGT CC-3'-P |
| CT-TET | SEQ ID NO: 13 5'TET CA AAA CGC TTA TTT TGC TAG TGG CC 3'-P |
| CP-HEX | SEQ ID NO: 14 5'HEX GG TAC AAA CTC CAA AAC TTC TTC CA 3'-P |
| CG-FAM | SEQ ID NO: 15 5'FAM TA GGT TTT ACC AAC TCG GTG TT GAT-3'-P |
| CK-TET | SEQ ID NO: 16 5'TET AG TGG CCC GAG CGA ACT AGA CTT TT 3'-P |

TABLE 2

Identification of Candida species in BacT/Alert blood culture bottles by TaqMan ® PCR

| Routine culture and ID | | TaqMan ® detection of PCR product | |
|---|---|---|---|
| Reported as: | No | Identified as: | No |
| C. albicans | 23 | C. albicans | 23 |
| C. glabrata | 18 | C glabrata | 17 |
| C. krusei | 6 | C. krusei | 6 |
| C. tropicalis | 6 | C. tropicalis | 5 |
| C. parapsilosis | 5 | C. parapsilosis | 4 |
| C. glabrata + C. albicans | 3 | C. glabrata + C. albicans | 2 |
| | | C. glabrata only | 1 |
| Total | 61 | | 57/61 (93.4%) |

TABLE 4

Sensitivity/specificity of the All-CAN-TET probe used in the TaqMan ® PCR assay

| Genomic DNA tested | Delta RO values (Mean ± SE)[a] |
|---|---|
| C. pseudotropicalis | 4.59 ± 0.16[b] |
| C. parapsilosis | 4.59 ± 0.16[b] |
| C. krusei | 4.56 ± 0.38[b] |
| C. albicans | 4.36 ± 0.10[b] |
| C. glabrata | 3.33 ± 0.18[b] |
| C. tropicalis | 3.27 ± 0.02[b] |
| S. cerevisiae | 2.27 ± 0.17[b] |
| C. guilliernondii | 2.18 ± 0.09[b] |
| A. fumigatus | 1.66 ± 0.18[b] |
| A. flavus | 1.13 ± 0.18[b] |
| H. capsulatum | 0.21 ± 0.04 |
| P. aeruginosa | 0.19 ± 0.06 |

TABLE 3

Identification of Candida spp. in positive blood cultures by TaqMan ® PCR using multiple fluorescent probes
Mean delta RQ ± SD

| | PCR USING: | | | | | |
|---|---|---|---|---|---|---|
| | PCR "A" Three probes | | | PCR "B" Two probes | | PCR "C" One probe |
| | CA-FAM | CT-TET | CP-HEX | CG-FAM | CK-TET | All-CAN-TET |
| C. albicans (n = 23) | 0.95 ± 0.62 | 0.07 ± 0.06 | 0.09 ± 0.10 | 0.01 ± 0.01 | 0.02 ± 0.02 | 3.42 ± 0.67 |
| C. tropicalis (n = 6) | 0.03 ± 0.04 | 0.48 ± 0.38 | 0.07 ± 0.06 | 0.02 ± 0.02 | 0.03 ± 0.03 | 1.92 ± 1.34 |
| C. parapsilosis (n = 5) | 0.03 ± 0.03 | 0.02 ± 0.02 | 0.33 ± 0.12 | 0.01 ± 0.01 | 0.01 ± 0.02 | 1.78 ± 1.48 |
| C. glabrata (n = 18) | 0.01 ± 0.02 | 0.03 ± 0.04 | 0.03 ± 0.05 | 0.63 ± 0.39 | 0.01 ± 0.02 | 2.81 ± 1.24 |
| C. krusei (n = 6) | 0.02 ± 0.03 | 0.01 ± 0.03 | 0.07 ± 0.05 | 0.01 ± 0.02 | 0.73 ± 0.33 | 3.38 ± 0.92 |
| No growth (n = 10) | 0.02 ± 0.02 | 0.01 ± 0.01 | 0.04 ± 0.05 | 0.01 ± 0.01 | 0.04 ± 0.03 | 0.05 ± 0.05 |
| Bacteremia (n = 10) | 0.02 ± 0.02 | 0.01 ± 0.03 | 0.01 ± 0.02 | 0.01 ± 0.01 | 0.03 ± 0.03 | 0.07 ± 0.07 |

Notes: Mean ± SD for all control samples for CA-FAM probe (n = 55) = 0.02 ± 0.023, for CT-TET probe (n = 72) = 0.03 ± 0.048, for CP-HEX probe (n = 73) = 0.05 ± 0.070, for CG-FAM probe (n = 60) 0.01 ± 0.012, for CK-TET probe (n = 72) = 0.02 ± 0.029.

TABLE 4-continued

Sensitivity/specificity of the All-CAN-TET probe used
in the TaqMan ® PCR assay

| Genomic DNA tested | Delta RO values (Mean ± SE)[a] |
|---|---|
| E. coli | 0.18 ± 0.05 |
| C. neoformans | 0.17 ± 0.06 |
| P. marneffei | 0.16 ± 0.05 |
| Human cell line | 0.12 ± 0.09 |
| B. dermatitidis | 0.11 ± 0.11 |
| S. aureus | 0.06 ± 0.05 |

[a]Data for triplicate tubes from 1 to 3 experiments
[b]Positive value based on cutoff value criterion

TABLE 5

Comparative sensitivity of fluorescent TaqMan ® PCR, colorimetric PCR-EIA
and EtBr staining to detect C. albicans DNA from blastoconidia spiked into
BacT/Alert blood culture bottles containing rabbit's blood

| No of C. albicans per 200 µl | TaqMan ® PCR Mean Fluorescence + SD[A] | | PCR-EIA Mean A$_{650nm}$ + SD[A] | EtBr Staining of Agarose Gel |
|---|---|---|---|---|
| | All-CAN-TET | CA-FAM | CA-DIG | |
| $10^5$ | 3.100 ± 0.450[b] | 1.140 ± 0.400[b] | 0.580 ± 0.050[b] | + |
| $10^4$ | 2.750 ± 0.180[b] | 0.690 ± 0.100[b] | 0.440 ± 0.060[b] | + |
| $10^3$ | 0.690 ± 0.120[b] | 0.190 ± 0.030[b] | 0.130 ± 0.030[b] | + |
| $10^2$ | 0.340 ± 0.070[b] | 0.070 ± 0.020[b] | 0.020 ± 0.010[b] | − |
| $10^1$ | 0.060 ± 0.030 | 0.040 ± 0.060 | 0.010 ± 0.001 | − |
| 0 | 0 | 0 | 0 | − |
| Purified C. albicans DNA (1 ng) | 4.380 ± 0.170[b] | 1.000 ± 0.080[b] | 0.550 ± 0.100[b] | + |

[A]Data from three experiments, duplicate wells per experiment.
[B]$P < 0.01$ or $P < 0.05$ by Student's t test versus mean for samples containing no DNA.

Throughout this application various publications are referenced within parentheses. Full citations for these publications may be found at the end of the specification immediately preceding the Sequence Listing. The disclosures of these publications in their entireties are hereby incorporated by reference into this application in order to more fully describe the state of the art to which this invention pertains.

REFERENCES

Armstrong, C. 1989. Problems in Management of Opportunistic Fungal Diseases. Rev. Infect. Dis. 2:S1591–S1599.

Barns, S. M., Lane, D. J., Sogin M. L., Bibeau, C. and Weisburg, W. G. (1991) Evolutionary relationships among pathogenic Candida species and relatives. J. Bacteriol. 173:2250–2255.

Buchman, T. G., M. Rosser, W. G. Merz, and P. Charache. 1990. Detection of surgical pathogens by in vitro DNA amplification. Part I. Rapid identification of Candida albicans by in vitro amplification of a fungus-specific gene. Surgery 108:338–347.

Dams, E., Hendriks, L., Van de Peer, Y., Neefs, J. and Smits, G. (1988) Compilation of small ribosomal subunit RNA sequences. Nucl. Acids Res. 16:r87–r174.

Devereux, J., Haeberli, P. and Smithies, O. (1984) A comprehensive set of sequence analysis programs for the VAX. Nucl. Acids Res. 12:387–397.

Edman, J. C., Kovacs, J. A., Masur, H., Santi, D. V., Elwood, H. J. and Sogin, M. L. (1988) Ribosomal RNA shows Pneumocystis carinii to be a member of the fungi. Nature (London). 334:519–522.

Felsenstein, J. (1982) Numerical methods for inferring evolutionary trees. Quart. Rev. Biol. 57:379–404.

Felsenstein, J. (1985) Confidence limits on phylogenies: an approach using the bootstrap. Evolution. 39:783–791.

Fujita et al. (1995) Microtitration Plate Enzyme Immunoassay to Detect PCR-Amplified DNA from Candida species in Blood. 33:962–967.

Glee, P. M., P. J. Russell, J. A. Welsch, J. C. Pratt, and J. E. Cutler. 1987. Methods of DNA extraction from Candida albicans. Anal. Biochem. 164:207–213.

Guthrie, C. and Fink, G. R. (1991) Guide to yeast genetics and molecular biology. Meth. Enzymol. 194:3–20.

Jones, J. M. 1990. Laboratory diagnosis of invasive candidiasis. Clin. Microbiol. Rev. 3:32–45.

Kafatos, F. C., C. W. Jones, and A. Efstraliadis. 1979. Determination of nucleic acid sequence homologies and relative concentrations by a dot blot hybridization procedure. Nucl. Acids Res. 3:1541–1552.

Lasker, B. A., J. M. Brown, and M. M. McNeil. 1992. Identification and epidemiological typing of clinical and environmental isolates of the genus Rhodococcus with use of a digoxigenin-labeled rDNA gene probe. Clin. Infect. Dis. 15:223–233.

Lasker, B. A., Carle, G. F., Kobayashi, G. S. and Medoff, G. (1989) Comparison of the separation of Candida albicans chromosome-sized DNA by pulsed-field gel electrophoresis techniques. Nucl. Acids Res. 17:3783–3793.

Lehmann, P. F., Lin, D. and Lasker, B. A. (1992) Genotypic identification and characterization of species and strains within the genus Candida by using random amplified polymorphic DNA. J. Clin. Micro. 30:3249–3254.

Lott et al. (1993) Nucleotide Sequence analysis of the 5.8S rDNA and adjacent ITS2 Region of Candida albicans and Related Species. Yeast 9:1199–1206.

Magee, B. B., D'Souza, T. M. and Magee, P. T. (1987) Strain and species identification by restriction fragment length polymorphisms in the ribosomal DNA repeat of Candida species. J. Bacteriol. 169:1639–1643.

Messing, J., Crea, R. and Seeburg, P. H. (1981) A system for shotgun DNA sequencing. Nucl. Acids Res. 9:309–319.

Mitchell, T. G., White, T. J. and Taylor, J. W. (1992) Comparison of 5.8S ribosomal DNA sequences among the basidiomycetous yeast genera Cystofilobasidium, Filobasidium and Filobasdiella. J. Med. Vet. Mycol. 30:207–218.

Miyakawa, Y., T. Mabuchi, K. Kagaya, and Y. Fukagawa. 1992. Isolation and detection of Candida albicans by polymerase chain reaction. J. Clin. Micro. 30:894–900.

Needleman, S. B. and Wunsch, C. D. (1970) A general method applicable to the search for similarities in the amino acid sequence of two proteins. *J. Mol. Biol.* 48:443–453.

Odds, F. C. 1988. Candida and Candidosis: A Review and Bibliography, 2nd Ed., Philadelphia: Bailere Tindall.

O'Donnell, K. (1992) Ribosomal DNA internal transcribed spacers are highly divergent in the phytopathogenic ascomycete *Fusarium sambucinum* (*Gibberella pulicaris*). *Curr. Genet.* 22:213–220.

Ruano, G. W., W. Tenton, and K. K. Kidd. (1989). Biphasic amplification of very dilute DNA samples via "booster" PCR. *Nucl. Acids Res.* 3:5407–5411.

Saiki, K. K., D. H. Gelfand, S. Stafford, S. J. Scharf, R. Higuchi, G. F. Horn, K. B. Mullis, and H. A. Erlich. (1988). Primer directed enzymatic amplification of DNA with thermostable DNA polymerase. *Science* 239:487–491.

Sambrook, J., Fritsch, E. F. and Maniatis, T. Molecular Cloning: A laboratory manual. Cold Spring Harbor Laboratory Press. Cold Spring Harbor, N.Y. 1989.

Sanger, F., Nicklen, S. and Coulson, A. R. (1977) DNA sequencing with chain-terminating inhibitors. *Proc. Natl. Acad. Sci. USA.* 74:5463–5467.

Smith, L. M., Sanders, J. Z., Kaiser, R. J., Hughes, P., Dodd, C., Connell, C. R., Heiner, C., Kent, S. B. H. and Hood, L. E. (1986) Fluorescence detection in automated DNA sequence analysis. *Nature* (London). 321:674–679.

Telenti, A., G. R. Roberts. 1989. Fungal blood cultures. *Eur. J. Clin. Microbiol. Infect. Dis.* 8:151–156.

Thrash-Bingham, C., and Gorman, J. A. (1992) DNA translocations contribute to chromosome-length polymorphisms in *Candida albicans*. *Curr. Genet.* 22:93–100.

Thuring, R. W. J., J. P. Sanders, and P. Borst. 1975. A freeze squeeze method for recovering long DNA from agarose gels. *Anal. Biochem.* 66:213–220.

Van der Walt, J.P. and Yarrow, D. (1984) Methods for the Isolation, maintenance, classification and identification of yeasts. in Kreger-van Rij, N. J. W. (Ed). The yeasts: A taxonomic study. Elsevier, Amsterdam. pp. 45–104.

White, T. J., Bruns, T. D., Lee S. B. and Taylor, J. W. (1990) Amplification and direct sequencing of fungal ribosomal RNA genes for phylogenetics. in Innis, M. A., Gelfand, D. H., Sninsky, J. J. and White, T. J. (Eds). PCR Protocols. A guide to methods and applications. Academic Press, San Diego. pp. 315–322.

What is claimed is:

1. An isolated nucleic acid consisting essentially of the nucleotide sequence of SEQ ID NO: 11 or its complement and which hybridizes with nucleic acid obtained from a multiplicity of Candida or Aspergillus species.

2. An isolated nucleic acid consisting essentially of 8 to 35 nucleotides probe that specifically hybridizes with the isolated nucleic acid of claim 1 and which contains at least the first four bases of the sequence in claim 1 or the complement thereof.

3. An isolated nucleic acid of claim 2 that specifically hybridizes to a nucleotide sequence selected from the group of sequences consisting of SEQ ID NOS: 5–9.

4. A kit for the detection of Candida or Aspergillus species comprising a nucleic acid probe of claim 2 and instructions for the detection method.

5. An isolated nucleic acid as in claim 3, wherein the nucleotide sequence is selected from the group of sequences consisting of SEQ ID NOS: 12–16.

6. A kit as in claim 4, wherein the species detected is of the genus Candida.

7. A kit as in claim 6, wherein the kit contains at least one nucleic acid probe that specifically hybridizes to a nucleotide sequence selected from the group consisting of SEQ ID NOS: 5–9.

8. A kit as in claim 7, wherein the nucleic acid probe is further selected from a nucleic acid of the group consisting of SEQ ID NOS: 12–16.

9. A method for detecting Candida or Aspergillus species in a biological sample comprising the steps of:

(a) collecting a biological sample containing a Candida or Aspergillus species, (b) isolating nucleic acid from the biological sample, (c) amplifying a region of the nucleic acid using at least one fungal specific primer selected from the group consisting of SEQ ID NOS: 1–4, (d) detecting the amplified nucleic acid region, and (e) identifying the Candida or Aspergillus species.

10. The method as in claim 9, wherein the amplified region of the nucleic acid specifically hybridizes to the nucleic acid of claim 1.

11. The method as in claim 9, wherein the amplified region of the nucleic acid specifically hybridizes to a nucleotide sequence selected from the group consisting of SEQ ID NOS: 5–9.

12. The method as in claim 9, wherein the amplified region of the nucleic acid specifically hybridizes to a nucleotide sequence selected from the group consisting of SEQ ID NOS: 12–16.

13. The method as in claim 9, wherein the amplifying step includes the primers selected from SEQ ID NOS: 1 and 4, and a nucleic acid selected from the group SEQ ID NOS: 11–16.

14. The method as in claim 9, wherein the amplifying step includes the fungal specific primers of SEQ ID NOS: 2 and 3, and a nucleic acid selected from the group SEQ ID NOS: 11–16.

* * * * *

UNITED STATES PATENT AND TRADEMARK OFFICE
CERTIFICATE OF CORRECTION

PATENT NO.   : 6,235,890 B1
DATED        : May 22, 2001
INVENTOR(S)  : Christine J. Morrison, Ph.D., Errol Reiss, Brian Holloway and Jong Hee Shin It is certified that error appears in the above-identified patent and that said Letters Patent is hereby corrected as shown below:

Column 20,
Line 3, "(b23" should read -- (23 --.
Line 22, "Table 2). Sensitivity and specificity of the All-CAN-TET probe" should read -- + Table 2). ¶ Sensitivity and specificity of the All-CAN-TET probe --.

Column 23,
Table 5, "$^A$data" should read -- a Data --; "$^B$P" should read -- b P --.

Column 31,
Lines 18-19, change "consisting essentially of 8 to 35 nucleotides probe" to -- probe consisting essentially of 8 to 35 nucleotides --.

Signed and Sealed this

Twenty-eighth Day of May, 2002

Attest:

*Attesting Officer*

JAMES E. ROGAN
*Director of the United States Patent and Trademark Office*